(12) United States Patent
Jiao et al.

(10) Patent No.: US 7,345,218 B1
(45) Date of Patent: Mar. 18, 2008

(54) AGROBACTERIUM-MEDIATED TRANSFORMATION OF COTTON WITH NOVEL EXPLANTS

(75) Inventors: Gai-Li Jiao, Singapore (SG); Jian-Wei Liu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 0 days.

(21) Appl. No.: 09/936,173

(22) PCT Filed: Mar. 10, 1999

(86) PCT No.: PCT/SG99/00016

§ 371 (c)(1), (2), (4) Date: Jan. 18, 2002

(87) PCT Pub. No.: WO00/53783

PCT Pub. Date: Sep. 14, 2000

(51) Int. Cl.
  A01H 5/00 (2006.01)
(52) U.S. Cl. .................................................. 800/294
(58) Field of Classification Search ................ 800/294, 800/314; 536/23.1; 435/430, 430.1
  See application file for complete search history.

(56) References Cited

U.S. PATENT DOCUMENTS 4,672,035 A  6/1987 Davidonis et al.

FOREIGN PATENT DOCUMENTS

| EP | 0 270 355 B1 | 6/1988 |
| EP | 0 317 511 A3 | 5/1989 |
| WO | WO 89/05344 A1 | 6/1989 |
| WO | WO 97/12512 A2 * | 4/1997 |
| WO | WO 98/15622 A1 | 4/1998 |

OTHER PUBLICATIONS (Hansen et. al., 1999, Trends in plant Science, vol. 4, pp. 226-231, see p. 230).*

Firoozabady, et al., "Transformation of Cotton (*Gossypium hirsutum* L.) by *Agrobacterium tumefaciens* and Regeneration of Transgenic Plants," *Plant Molecular Biology*, 1997; vol. 10, pp. 105-116.

Hui, et al., "Studies on the Application of Multi-effect-triazole in Another Culture in Wheat," *Acta Agronomica Sinica*, 1997; vol. 23, No. 2, pp. 220-225. (Abstract).

Chen, et al., "Studies on the physiological effect of ABT No. 4 on cotton," *Acta Agriculturae Shangai*, 1994; vol. 10, No. 1, pp. 73-77. (Abstract).

Pan, et al., "A Study on the effect of MET on Regulating the Growth of Plantlet from Rice Pollen," *Acta Agriculturae Universitatis Jiangxiensis*, 1993; vol. 15, No. 3, pp. 225-229.

Sankhla, et al., "Influence of Growth Regulators on Somatic Embryogenesis, Plantlet Regeneration, and Post-transplant Survival of Echinochloa Frumentacea," *Plant Cell Rep.*, 1992; vol. 11, No. 7, pp. 368-371. (Abstract).

Lu, et al., "Study on Tissue and Protoplast Culture of Wild Cotton," *Acta Bot Sin*, 1991; vol. 33, No. 2, pp. 98-103. (Abstract).

Zhao, et al., "Effect of MET on Immature Embryo Callus Induction Differentiation and Hardening of Plants," *Acta Bot Sin*, 1990; vol. 32, No. 5, pp. 407-409. (Abstract).

Valvekens, et al., "*Agrobacterium tumefaciens*-mediated transformation of *Arabidopsis thaliana* root explants by using kanamycin selection," *Proc. Natl. Acad. Sci. USA*, 1988; vol. 85, pp. 5536-5540.

Trolinder, et al., "Somatic Embryogenesis and Plant Regeneration in Cotton (*Gossypium hirsutum* L.)," *Plant Cell Reports*, 1987; vol. 6, No. 3, pp. 231-234.

* cited by examiner

*Primary Examiner*—Anne Marie Grunberg
*Assistant Examiner*—Cathy Kingdon Worley
(74) *Attorney, Agent, or Firm*—Rothwell, Figg, Ernst & Manbeck p.c.

(57) ABSTRACT

A method is disclosed for producing a transgenic cotton plant comprising the steps of (a) obtaining cottonfibrous root explants, (b) culturing the fibrous root explants to induce callus formation, (c) exposing root callus to a culture of *Agrobacterium tumefaciens* that harbors a vector comprising an exogenous gene and a selectable marker, the *Agrobacterium* being capable of effecting the stable transfer of the exogenous gene and selection agent resistance gene to the genome of the cells of the explant, (d) culturing the callus in the presence of the selection agent to which the selection agent resistance gene confers resistance so as to select for transformed cells, (e) inducing somatic embryo formation in the selected callus culture, and (f) regenerating the induced somatic embryos into whole transgenic cotton plants.

31 Claims, 2 Drawing Sheets

AGROBACTERIUM-MEDIATED TRANSFORMATION OF COTTON WITH NOVEL EXPLANTS

TECHNICAL FIELD

The present invention relates to the general field of genetic engineering of plants, in particular to the introduction of exogenous genetic material into cotton by *Agrobacterium* transformation of novel explants followed by somatic embryo regeneration.

BACKGROUND

Cotton is the most extensively used natural fiber in the textile industry. Its annual production worldwide is over 100 million bales, valued at US$45 billion. Cotton lint or seed hair is a terminally differentiated single epidermal cell from 50 species of the genus *Gossypium* of the family Malvaceae. It is classified as a natural, cellulosic, monocellular and staple fiber. The cultivated cotton varieties, which have been cultivated for more than 5000 years, all come from two diploids (2n=2x=26) (*G. herbaceum* and *G. arboreum*) and two allotetraploids (2n=4x=52) (*G. hirsutum* L., Upland; and *G. barbadense* L., Sea Island). In 1997 the top five world cotton producers were the United States, China, India, Pakistan and Uzbekistan, producing about 63 million bales.

In the next century, most crops, including cereals, oil crops, fruits, vegetables and other economically important crops, will be genetically engineered with added or modified traits ranging from improvement of yield and quality, to herbicide resistance and pest resistance (Chappell, 1996; Fraley et al., 1986; Herrera-Estrella et al., 1983; Hoekema et al., 1983; Horsch et al., 1985; Jefferson, 1987; Ryals, 1996). In cotton, the new technology will be used to increase yield, improve fiber quality and create new varieties which are resistant to herbicides, pest insects, nematodes and diseases (John, 1996; John & Keller, 1996; John & Stewart, 1992; Murray et al., 1993; Rajasekaran et al., 1996; Schell, 1997; Stewart, 1992).

1. Tissue Culture of Cotton: In 1935, Skovsted reported the first embryo culture of cotton. Beasley (1971) reported callus formation in cotton as an outgrowth from the micropylar end of fertilized ovules on MS medium. Somatic embryogenesis was achieved from a suspension culture of *G. klotzschianum* (Prive & Smith, 1979). In 1983, Davidonis & Hamilton first succeeded in efficient and repeatable regeneration of cotton (*G. hirsutum* L.) plants from callus after two-year cultivation. Cotton plants were since regenerated through somatic embryogenesis from different explants (Zhang & Feng, 1992; Zhang, 1994) including cotyledon (Davinonis et al., 1987; Davidonis & Hamilton, 1983; Finer, 1988; Firoozabady et al., 1987), hypocotyl (Cousins et al., 1991; Rangan & Zavala, 1984; Rangan & Rajasekaran, 1996; Trolinder & Goodin, 1988; Umbeck et al., 1987, 1989), stem (Altman et al., 1990; Finer & Smith, 1984), shoot apex (Bajaj et al., 1985; Gould et al., 1991; Turaev & Shamina, 1986), immature embryo (Beasley, 1971; Eid et al., 1973; Stewart & Hsu, 1977, 1978), petiole (Finer & Smith, 1984; Gawel et al., 1986; Gawel & Robacker, 1990), leaf (Finer & Smith, 1984; Gawel & Robacker, 1986), root (Chen & Xia, 1991; Kuo et al., 1989), callus (Finer & McMullen, 1986; Trolinder et al., 1991) and protoplast (Chen et al., 1989).

2. Cotton Transformation: Explants (such as hypocotyl, cotyledon, callus generated from hypocotyl and cotyledon, as well as immature embryos) have been used for *Agrobacterium*-mediated transformation and particle bombardment (de Framond et al., 1983; Finer & McMullen, 1990; Firoozabady et al., 1987; Perlak et al., 1990; Rangan & Rajasekaran, 1996; Rajasekaran et al., 1996; Trolinder et al., 1991; Umbeck et al., 1987, 1989, 1992). In addition, meristematic tissue of excised embryonic axes has also been used for cotton transformation by particle bombardment (Chlan et al., 1995; John, 1996; John & Keller, 1996; McCabe & Martinell, 1993). Zhou et al. (1983) transformed cotton by injecting DNA into the axile placenta one day after self-pollination. However, cotton transformation is highly dependent on genotype (Trolinder, 1985a, 1985b, 1986; Trolinder & Goodin, 1987, 1988a, 1988b). Apart from a few cultivars which are regeneratable and transformable, such as *Gossypium hirsutum* cv. Coker 312 and *G. hirsutum* Jin 7, most other important elite commercial cultivars, such as *G. hirsutum* cv. D&P 5415 and *G. hirsutum* cv. Zhongmian 12, are not regeneratable and transformable by these methods.

Based on previous reports and the inventor's own experimental data, high efficiency of callus induction (60%) can be achieved using the hypocotyl as an explant. However, the transformation rate was only 20% (Firoozabady et al., 1987; Umbeck et al., 1987). Several factors can lead to breakthrough of nontransformed calli, or to chimeric calli consisting of predominantly nontransformed cells: (1) low kanamycin levels (a high level of kanamycin is toxic to cotton explants and calli); (2) experience-dependent selection in later stages of callus proliferation; and (3) use of explants such as the hypocotyl which has only partial contact with the selective media (Firoozabady et al., 1987). When the cotyledon was used as an explant, although the transformation rate was higher than that with the hypocotyl, it was often difficult to eliminate *Agrobacterium* during subsequent culture (Jiao G.-L and Chen, Z.-X., personal communication; Umbeck et al., 1987, 1989). The transformation rate of meristemic tissue through particle bombardment was simply too low (0.02%-0.22%) compared to that of *Agrobacterium* mediated transformation.

There thus remains a need for methods of producing transgenic cotton plants that provide high rates of transformation along with high rates of transformants among regenerated somatic embryos.

SUMMARY OF THE INVENTION

The present invention relates to a method for producing transgenic cotton plants, comprising the steps of (a) obtaining cotton fibrous root explants, (b) culturing the fibrous root explants to induce callus formation, (c) exposing root callus to a culture of *Agrobacterium tumefaciens* that harbors a vector comprising an exogenous gene and a selectable marker, the *Agrobacterium* being capable of effecting the stable transfer of the exogenous gene and selection agent resistance gene to the genome of the cells of the explant, (d) culturing the callus in the presence of the selection agent to which the selection agent resistance gene confers resistance so as to select for transformed cells, (e) inducing somatic embryo formation in the selected callus culture, and (f) regenerating the induced somatic embryos into whole transgenic cotton plants.

The present method provides for an improved rate of transformation when compared to previous methods that employ hypocotyl and cotyledon tissue. The method is believed to have wide applicability to a variety of cotton varieties.

DETAILED DESCRIPTION

Figure 1:
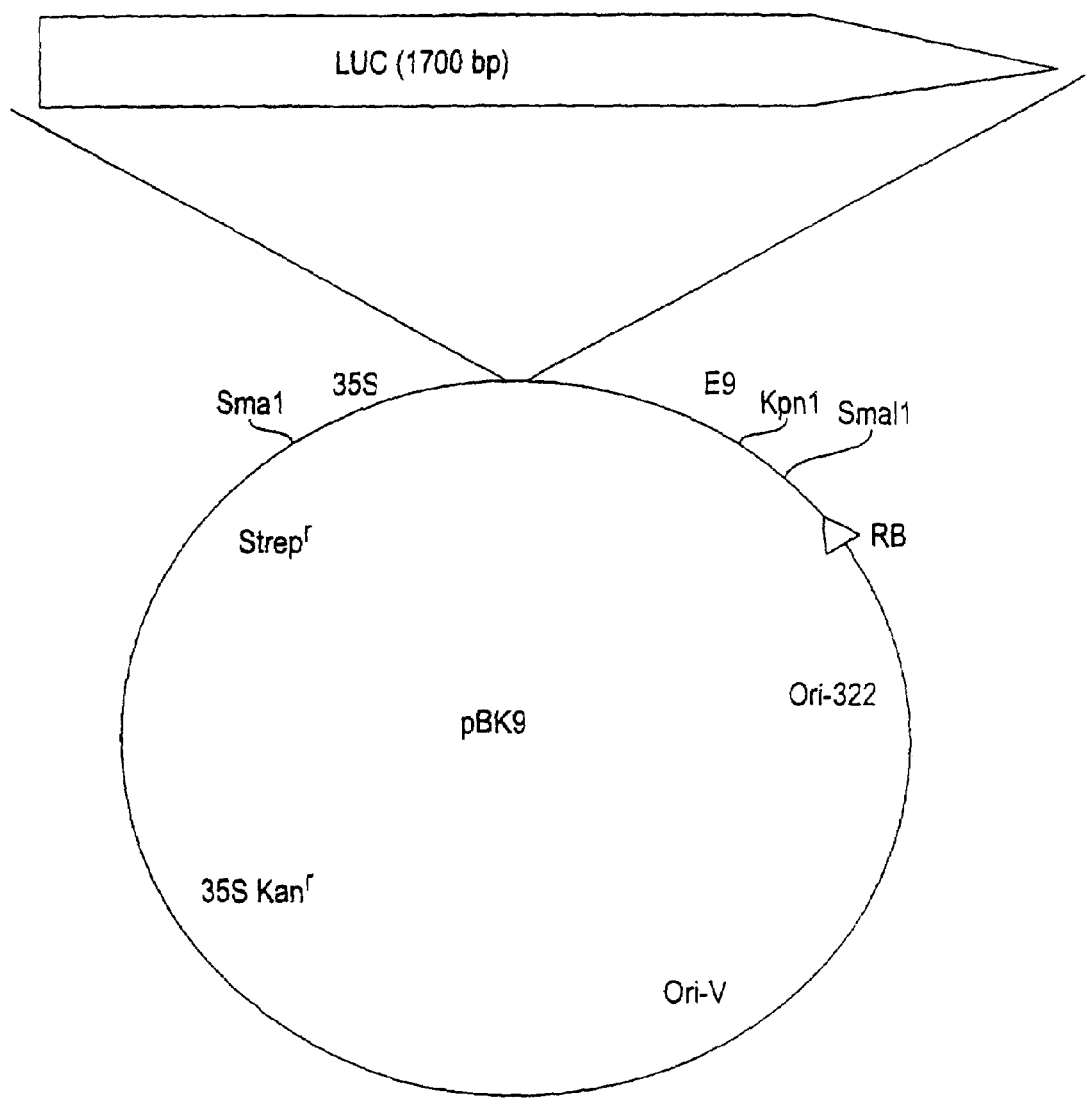
FIG. 1 shows the plasmid pBK9, containing a luciferase gene used to detect positive transformants obtained by the methods of the present invention.

In order to overcome the problems seen with prior art methods and increase the efficiency of transformation, fibrous root explants were used for *Agrobacterium*-mediated transformation of cotton. Although in *Arabidopsis* high efficiency of transformation was achieved in *Agrobacterium*-mediated transformation with fibrous root explants (Valvekens, et al., 1988), and the differentiation of young fibrous roots from cotton on MS medium containing 2.0 mg/L IAA, 0.02-0.04 mg/L IBA has been reported (Kuo, C. C., et al., 1989), there is no report in the literature about using fibrous roots as explants for cotton transformation.

Fibrous roots now have been successfully used as explants for *Agrobacterium*-mediated transformation and plant regeneration. In the process modified media for seedling culture, and regeneration and differentiation of embryogenic calli were used.

Media used to culture seedlings to obtain explant material was designed to minimize browning of the roots (browning adversely effects the ability of explants to grow in culture and form callus), and to promote overall vigorous root growth. In one embodiment MET (multi-effect triazole a chemical agent used in agriculture to promote root growth) is used in the seedling culture medium. In a preferred embodiment MET and NAA (α naphthalene acetic acid) are used together in the seedling culture medium to reduce the proportion of browned roots and increase callus initiation rate. MET is preferably used in concentrations ranging from about 0.05 mg/l to about 0.2 mg/l, most preferably about 0.1 mg/l. NAA is preferably used in concentrations ranging from about 0.01 mg/l to about 0.2 mg/l, most preferably about 0.05 mg/l. MET and NAA are also preferably used in the medium used to root transgenic seedlings regenerated from callus, in amounts similar to those described for the seedling culture medium. In a preferred embodiment of the callus-forming medium vitamin $B_5$, 2,4-D ((2,4-dichlorophenoxy)acetic acid, $MgCl_2$ and glucose are used, preferably about 0.05 mg/l to about 0.15 mg/l 2,4-D, about 0.4 mg/l to about 1.2 mg/l $MgCl_2$, and about 1% to about 5% glucose, most preferably about 0.1 mg/L 2,4-D, 0.8 mg/L $MgCl_2$ and 3% glucose. In an alternate preferred embodiment of the callus-forming medium myo-inositol, vitamin $B_1$, and dimethylallyl(amino)purine are used, a, preferably about 50 mg/l to about 150 mg/l myo-inositol, about 1 mg/l to about 10 mg/l vitamin $B_1$, and about 0.1 mg/l to about 7.5 mg/l dimethylallyl(amino)purine, most preferably about 100 mg/l myo-inositol, about 0.4 mg/l vitamin $B_1$ and about 5 mg/l dimethylallyl(amino)purine. The same media used for callus induction can also be used during selection with antibiotics—for example with 300-400 mg/L cefotaxime or 15-30 mg/L kanamycin. The presence of high concentrations (preferably about 1900 mg/l to about 5700 mg/l, most preferably about 3800 mg/L) of nitrates was crucial for the observed effectiveness of the differentiation medium. With the fibrous roots as explants, although the rate of callus-induction was lower compared with hypocotyl and cotyledon, a higher rate of transformation was achieved.

Techniques for introducing exogenous genes into *Agrobacterium* such that they will be transferred stably to a plant or plant tissue exposed to the *Agrobacterium* are well-known in the art and do not form part of the present invention. It is advantageous to use a so-called "disarmed" strain of *Agrobacterium* or Ti plasmid, that is, a strain or plasmid wherein the genes responsible for the formation of the tumor characteristic of the crown gall disease caused by wild-type Agrobacterium are removed or deactivated. Numerous examples of disarmed *Agrobacterium* strains are found in the literature (e.g., pAL4404, pEHA101 and pEH 105 (Walkerpeach & Veltern, 1994)). It is further advantageous to use a so-called binary vector system, such as that described in U.S. Pat. Nos. 4,940,838 and 5,464,763 (Schilperoort, et al.) and Hoekema et al., 1983. A binary vector system allows for manipulation in *E. coli* of the plasmid carrying the exogenous gene to be introduced into the plant, making the process of vector construction much easier to carry out.

Similarly, vector construction, including the construction of chimeric genes comprising the exogenous gene that one desires to introduce into the plant, can be carried out using techniques well-known in the art and does not form part of the present invention. Chimeric genes should comprise promoters that have activity in the host in which expression is desired. For example, it is advantageous to have a series of selectable markers for selection of transformed cells at various stages in the transformation process. A selectable marker (for example a gene conferring resistance to an antibiotic such as kanamycin, cefotaxime or streptomycin) linked to a promoter active in bacteria would permit selection of bacteria containing the marker (i.e., transformants). Another selectable marker linked to a plant-active promoter, such as the CaMV 35S promoter or a T-DNA promoter such as the NPT II NOS promoter, would allow selection of transformed plant cells. The exogenous gene that is desired to be introduced into the plant cell should comprise a plant-active promoter in functional relation to the coding sequence, so that the promoter drives expression of the gene in the transformed plant. Again, plant-active promoters, such as the CaMV 35S, the NPT II NOS promoter or any of a number of tissue-specific promoters, are well-known in the art and selection of an appropriate promoter is well within the ordinary skill in the art.

The present method can be used to produce transgenic plants expressing any number of exogenous genes, and is not limited by the choice of such a gene. The selection of the desired exogenous gene depends on the goal of the researcher, and numerous examples of desirable genes that could be used with the present invention are known in the art (e.g., the family of *Bacillus thuringiensis* toxin genes, herbicide resistance genes such as shikimate synthase genes that confer glyphosate resistance, U.S. Pat. No. 5,188,642, or a 2,4-D monooxygenase gene that confers 2,4-D resistance, Bayley et al., *Theoretical and Applied Genetics*, vol. 82, pp. 645-49, male sterility genes such as the antisense genes of U.S. Pat. No. 5,741,684 (Fabijanski, et al.), or even the elaborate crop protection systems described in U.S. Pat. No. 5,123,765 (Oliver, et al.)).

*Agrobacterium*-mediated cotton transformation is considered in the art to be heavily variety-dependant. The Coker series of cotton varieties have been shown to be relatively easy to transform. However, DP 5412, Zhongmian 12 and many other varieties still have difficulties associated with transformation. The situation is the same for *G. barbadense* and other diploid species. Particle bombardment, DNA injection and infection of meristem tissue with *Agrobacterium* are some alternative methods, which can be used to transform, in theory, all the cotton varieties. The problems associated with these methods are: low efficiency of transformation and unstable/unreliable results. It is believed that the present method has broad applicability to transformation of cotton varieties, as it overcomes or minimizes several of the problems associated with previous work relating to cotton transformation (such as breakthrough of non-transformed callus, poor explant growth and low transformation rate, poor somatic regeneration) through the use of fibrous root explants.

The following abbreviations are used to designate culture media useful in connection with the present invention:

LB medium (10 g bacto-tryptone+5 g bacto-yeast extract+ 10 g NaCl);
B5 medium (Gamborg et al., 1968; Sigma, Cat. No. G-5768);
MS medium (Murashige et al., 1962; Sigma, Cat. No. M-5524);
SH medium (Stewart & Hsu, 1977. *Planta* 137, 113-117);
CB-1.1 (½ MS+½ B5 Vitamin+0.1 mg/L NAA);
CB-1.2 (½ B5 medium);
CB-2.1 (MS macro+B5 micro+0.05 mg/L 2,4-D+0.1 mg/L kinetin+3% glucose+2 g/L gellan gum (PhytaGel™, Sigma)+0.93 mg/L $MgCl_2 \cdot 6H_2O$, pH5.8);
CB-2.2 (MS macro+100 mg/L myo-inositol+0.4 mg/L vitamin B1+5 mg/L 2iP (6-(γγ-dimethylallyl(amino)purine)+0.2 mg/L NAA+3% glucose+2 g/L gellan gum (PhytaGel™, Sigma)+0.93 mg/L $MgCl_2 \cdot 6H_2O$, pH5.8);
CB-3.1 (CB-2.1+500 mg/L cefotaxime+50 mg/L kanamycin);
CB-3.2 (CB-2.2+500 mg/L cefotaxime+50 mg/L kanamycin);
CB-4 (Modified CB-3.1 or CB-3.2 by adding double amount of $KNO_3$ and removing $NH_4NO_3$ with 250 mg/L cefotaxime and 20 mg/L kanamycin);
CB-5 (SH+1.5% Sucrose+2 g/L gellan gum (PhytaGel™, Sigma)+0.93 g/L $MgCl_2$, pH7.0).

The following Examples are intended to illustrate the present invention, and not in any way to limit its scope, which is solely defined by the claims.

EXAMPLE 1

Regeneration of Cotton Plants from Root Tissue Culture

Preparation of Root Explants: Cotton Seeds were sterilized in 70% ethanol for 10-15 min., and then treated with 10% $H_2O_2$ for 30-120 mins. Treated seeds were rinsed in sterile water for 24 hrs at 28° C. and germinated on either CB-1.1 medium or CB-1.2 medium at 28° C.-30° C., 16 h light (60-90 µE $m^{-2}$ $s^{-1}$) Seven to ten days sterile seedlings thus grown were used to prepare explants. It was found that plentiful healthy roots (longer and thicker) with white color were obtained using CB-1.1 medium, whereas shorter and thinner roots with grey to brown color were obtained using the CB-1.2 medium. Therefor, CB-1.1 was chosen for further work.

Induction of calli: Fibrous roots were cut from seedlings and cultured on CB-2.1 medium or CB-2.2 medium at 28° C.-30° C. for three days, 16 h light (60-90 µm² $s^{-1}$). The optimum size for root explants was 5-7 mm. A few small calli initiated on the cut sites of root segments in as little as 3 days. In general, transformed hypocotyl or cotyledon explants started to initiate callus on inducing medium after 3 days. However, previous to the present invention, transformed root explants were generally found to initiate callus only after 10 days of cultivation. The color of the root explants was white. One week later, small calli were also initiated from other parts of the root segments. The color of the root explants changed to grey or even brown. At the end of 2 weeks of cultivation, calli initiated from the whole root explants and grew well. Of the two inducing media, CB-2.2 was found to induce good callus formation, while CB-2.1 did not. On CB-2.2 medium, root explants grew well, and the microcallus initiated on the cut sites of the explant. About 10% of root explants initiated callus after only 3 days on the medium. On the other hand, while CB-2.1 medium supported the growth of the root explants well, there was no callus initiation on the cut sites. The efficiency of callus-induction with root explants on the CB-2.2 medium was 10%, which was lower than that with hypocotyl or cotyledon explants (20-30%). A summary of results showing callus induction and transformation efficiency appears in Table 1, below.

Regeneration of root calli: After one month, the calli were transferred to new medium for subculture on either CB-2.1 medium or CB-2.2 medium. After 2 months of subculture, the mature calli were transferred to CB-4 (without antibiotic) for induction of somatic embryos. Glutamine and L-asparagine were added in amounts of 0.5 mg/L and 0.2 mg/L, respectively, to promote embryogenesis. Primary somatic embryos were formed on the embryogenic calli after 2 months of cultivation, with 2 subcultures in between on the same media. Primary somatic embryos were subcultured on the same media for another month before mature somatic embryos were formed. Some of the somatic embryos developed to plantlets. These small plantlets were transferred to CB-5 medium for root induction. When the plantlets had made roots on the CB-5 medium (4-6 weeks), they were transferred to soil and maintained in an incubator under high humidity for 3-4 weeks at 28° C., 16 h light (60-90 µE $m^{-2}$ $s^{-1}$), and then transferred to large pots with soil in a green house.

EXAMPLE 2

*Agrobacterium* Transformation and Culture

Figure 2:
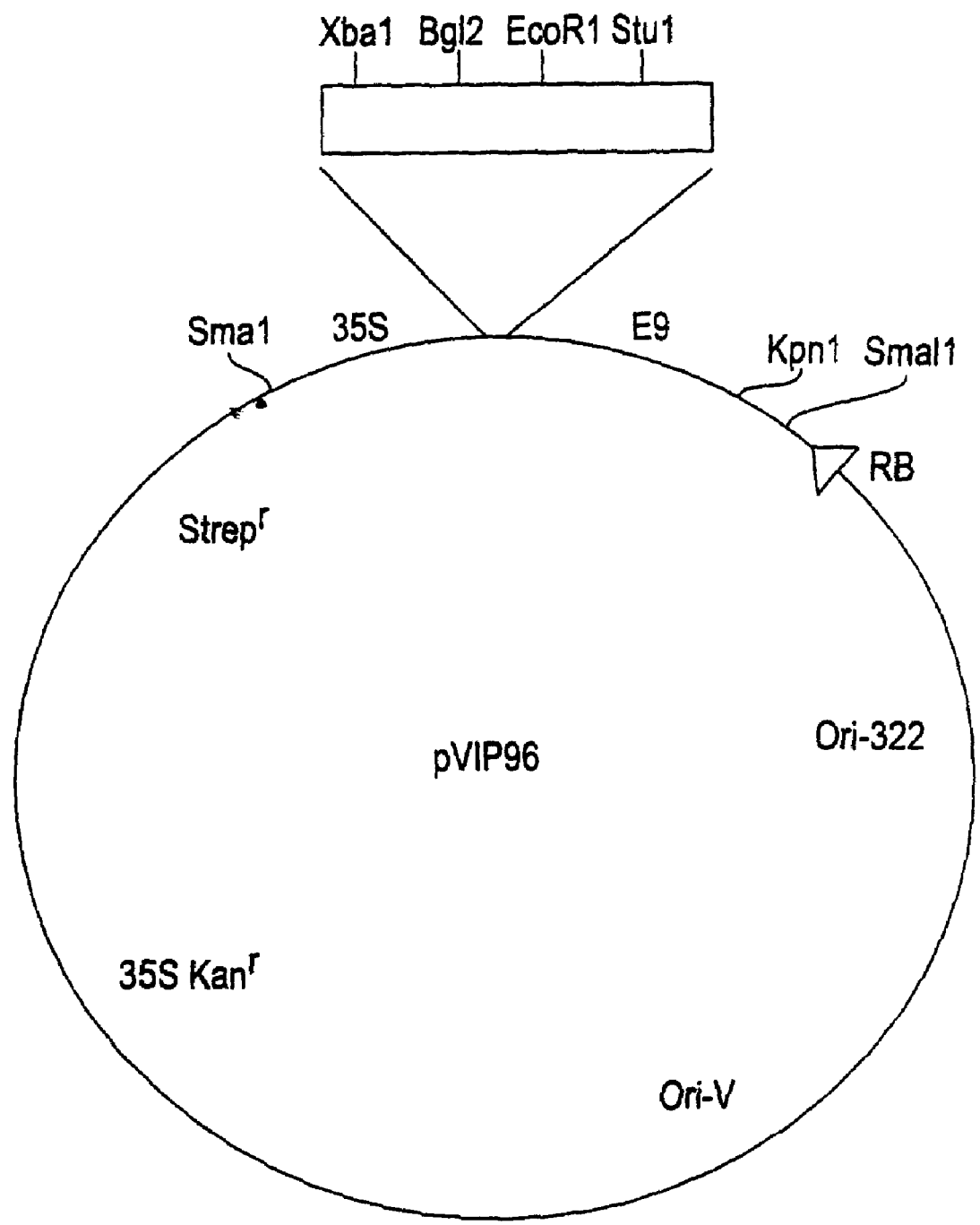
FIG. 2 shows the plasmid pVIP96, the plasmid from which pBK9 was derived by insertion of the luciferase gene.

The plasmid pBK9 (35S:LUC) (see FIG. 1) was generated by cloning the luc coding sequence from the BamHI/StuI fragment of plasmid pGEMluc into the blunt-ended StuI site of the plasmid pVIP96 (see FIG. 2).

Prepared competent cells (400 microliter) in Eppendorf tube from −80° C. were put on ice to thaw. Plasmid DNA was added in the cells. After gentle mixing, the mixture was incubated on ice for 45 minutes. The Eppendorf tube containing the mixture was put into liquid nitrogen for 1 minute and afterwards in a water bath (37° C.) for 3 minutes. After the incubation, 800 microliter LB medium (without antibiotics) was added into the mixture and the tube with the mixture was incubated at 28° C. for 3 hours. After a brief centrifugation at 12,000 rmp, 800 microliter supernatant was removed. The rest of the medium was mixed well with the cell pellet and the mixture was plated onto LB plates containing 100 mg/L kanamycin and 100 mg/L streptomycin. Successful transformed LBA4404 cells formed colonies on the plates in about 48 hours at 28° C. *Agrobacterium* strain LBA4404 harboring the plasmid pBK9 (35S:LUC) was initiated on LB plate with kanamycin (50 mg/L), streptomycin (50 mg/L) and refamycin (50 mg/L). A single colony was inoculated into LB liquid medium without antibiotics and grown overnight for about 18 h at 28° C. on a gyratory shaker. The optical density ($A_{600}$) value was adjusted to 0.1-0.4 in liquid LB medium prior to use.

EXAMPLE 3

Transformation of Root Explant Tissue and Regeneration of Transgenic Cotton Plants Root explants were obtained by cultivating sterile cotton seeds as described in Example 1, above, on CB-1.1 medium. Fibrous roots were cut from seedlings and cultured on CB-2.2 for two days, 16 h light (60-90 µE $m^{-2}s^{-1}$). The fibrous roots were then cut into small segments (5-10 mm) and incubated with the cell suspension culture of *Agrobacterium tumefaciens* strain LBA4404 harboring the plasmid pBK9 (35S:LUC) ($A_{600}$=0.1-0.6) of Example 2 for 15 min. After drainage of the bacterial solution, the root explants were cultured at 28° C., 16 h light (60-90 µE $m^{-2}s^{-1}$) for an additional two days. The optimum concentration of the *Agrobacterium* strain LBA4404 for root explants was lower ($A_{600}$=0.1-0.4) than that for hypocotyl and cotyledon explants ($A_{600}$=0.3-0.6). Optimal bacterial concentrations did not affect the growth of the root explants and the subsequent callus induction.

Co-cultured explants were washed twice with sterile distilled water and transferred to CB-3.1 medium or CB-3.2 medium for cultivation at 28° C., 16 h light (60-90 µE $m^{-2}s^{-1}$).

After four weeks, kanamycin-resistant calli were selected and subcultured on the same media for the second selection. At the same time, some of the calli were selected to detect the LUC expression with the luciferase luminescence image system (see Example 4, below). The process of inducing callus took about 2 months. The efficiency of callus induction from root explant was lower compared with that from hypocotyl and cotyledon explants.

Kanamycin-resistant calli were transferred to CB-4 medium to induce embryogenic calli and somatic embryos. After 4-6 weeks of cultivation, with one subculture, mature somatic embryos appeared on the calli. Plantlets developed afterwards from some of the embryos. The green plantlets were then transferred to rooting medium (CB-5) for root induction. When plantlets had made roots, they were transferred to soil and maintained in an incubator under high humidity for 3-4 weeks at 28° C., 16 h light (60-90 µE $m^{-2}$ $s^{-1}$), and then transferred to large pots with soil in a green house.

EXAMPLE 4

Detection of Luciferase Activity

Plant materials (such as callus, leaf and whole plantlet) were sprayed with a solution containing 0.5 mM potassium luciferin and 0.01% (w/v) polyoxyethylenesorbitan monolaurate (Tween-20) and left for 30 min. The luciferase luminescence from these plant materials was visualized using an image-intensifying camera and photon-counting image processors purchased from Prinston Instruments Inc., 3660 Quakerbridge Road, Trenton, N.J. 08619. The exposure time was 6 min. The electronic images were converted to Microsoft Powerpoint TIFF files and printed out from a standard color printer.

Callus growing on selected medium for one month was selected to test LUC expression with the video image system. The positive transformed callus had white spots whereas untransformed callus did not. Out of the 139 pieces of kanamycin resistant calli, 49 pieces were positive with LUC activity. The successful transformation rate was therefor 35%, which was much higher than that seen using cotyledon or hypocotyl as explant (20%).

TABLE 1

Brief summary of root as explant for transformation

| Variety | Construct | Conc. of Strain | Date of selected medium | No. of explant | No. of callus | No. of LUC test | No. of LUC+ |
|---|---|---|---|---|---|---|---|
| Coker 312 | 35S-LUC | 0.1-0.2 | 9/10/97 | 2574 | 156 | 16 | 12 |
|  | 35S-LUC | 0.43 | 23/10/97 | 1255 | 70 | 8 | 5 |
|  | 35S-LUC | 0.438 | 23/10/97 | 564 | 46 | 28 | 19 |
|  | 35S-LUC | 0.2-0.4 | 5/3/98 | 520 | 33 | 15 | 11 |

REFERENCES

Altman, D. W. et al. 1990. Economic Botany 40, 106.

Bajaj, Y. P. S. 1985. Theor. Appl. Genet. 70, 363.

Beasley, C. A. 1971. In vitro culture of fertilized cotton ovules. Biosci. 21, 906-7.

Chappell, J. 1996. Plant biotechnology comes of age—again. Mol. Breeding. 2, 1-6.

Chen, Z. X., Li, S. J., Yue, J. X., Jiao, G. L. and Liu S. X. 1989. Plantlet regeneration from protoplasts isolated from an embryogenic suspension culture of cotton (*Gossypium hirsutum* L.). Acta Botanica Sinica 31, 966-9.

Chen, Z. X. and Xia Z. A. 1991. Acta Botanica Sinica 33, 98.

Chlan, C. A., Lin, J., Cary, J. W. and Cleveland, T. E. 1995. A procedure for biolistic transformation and regeneration of transgenic cotton from meristematic tissue. Plant Mol. Biol. Rep. 13, 31-7.

Cousins, Y. L., Lyon, B. R. and Llewellyn, D. J. 1991. Transformation of an Australian cotton cultivar: prospects for cotton improvement through genetic engineering. Aust. J. Plant Physiol. 18, 481-94.

Davidonis, G. H., and Hamilton, R. H.1983. Plant regeneration from callus tissue of *Gossypium hirsutum* L. Plant Sci. Lett. 32, 89-93.

Davidonis, G. H., Mumma, R. O. and Hamilton, R. H. 1987. Controlled regeneration of cotton plants from tissue culture. U.S. Pat. No. 4,672,035.

de Framond et al. 1983. Mini-Ti: a new vector strategy for plant genetic engineering. Bio/technology 1, 262-9.

Finer, J. J. and Smith, R. H.1984. Initiation of callus and somatic embryos from explants of mature cotton (Gossypium klotzschianum Anderss). Plant Cell Reports 3, 41-43.

Finer, J., 1988. Plant regeneration from somatic embryogenic suspension cultures of cotton (*Gossypium hirsutum* L.). Plant Cell Rep. 7, 399-402.

Finer, J. J. and McMullen, M. D. 1990. Transformation of cotton (*Gossypium hirsutum* L.) via particle bombardment. Plant Cell Reports 8, 586-9.

Firoozabady, E., Deboer, D., Merlo, D., Halk, E., Amerson, L., Rashka, K. and Murray, E. 1987. Transformation of cotton (*Gossypium hirsutum* L.) by *Agrobacterium tumefaciens* and regeneration of transgenic plants. Plant Mol. Biol. 10, 105-16.

Fraley, R. T., Rogers, S. G. and Horsch, R. B. 1986. Genetic transformation in higher plants. CRC Cri. Rev. Plant Sci. 4, 1-46.

Gamborg, O., Miller, R. and Ojima, K. 1968. Exp. Cell Res. 50, 148.

Gawel, N. J., Rao, A. P. and Robacker, C. 1986. Somatic embryogenesis from leaf and petiole callus cultures of *Gossypium hirsutum* L. Plant Cell Reports 5, 4579.

Gawel, N. J. and Robacker, C. 1986. Plant Cell Rep. 5, 67.

Gawel, N. and Robacker, C. 1990. Genetic control of somatic embryogenesis in cotton petiole callus cultures. Euphytica 49, 249-53.

Gould, J., Banister, S., Hasegawa, O., Fahima, M. and Smith, R. H.1991. Regeneration of *Gossypium hirsutum* and *G. barbadense* from shoot apex tissues for transformation. Plant Cell Reports 10, 12-6.

Herrera-Estrella, L., Depicker, A., Van Montagu, M. and Schell, J. 1983. Expression of chimeric genes transferred into plant cells using a Ti-plasmid-derived vector. Nature 303, 209-13.

Hoekema et al. 1983. A binary plant vector strategy based on separation of Vir- and T-Region of the *Agrobacterium tumefaciens* Ti-plasmid. Nature 303, 179-80.

Horsch, R. B., Fry, J. E., Hoffmann, N. L., Eichholtz, D., Rogers, S. G. and Fraley, R. T. 1985. A simple and general method for transferring genes into plants. Sci. 227, 1229-31.

Jefferson, R. A. 1987. Assaying chimeric genes in plants: the GUS gene fusion system. Plant Mol. Biol. Rep. 5, 387-405.

John, M. E. 1996. Structural characterization of genes corresponding to cotton fiber mRNA, E6: reduced E6 protein in transgenic plants by antisense gene. Plant Mol. Biol. 30, 297-306.

John, M. E. and Keller, G. 1996. Metabolic pathway engineering in cotton: Biosynthesis of polyhydroxybutyrate in fiber cells. Proc. Natl. Acad. Sci. USA 93, 12768-73.

John, M. E., and Stewart, J. McD. 1992. Genes for jeans: biotechnological advances in cotton. Trends Biotechnol. 10, 165070.

Kuo, C. C. et al., 1989. Proc. Beltwide Cotton Prod. Res. Confs, 638.

McCabe, D. E. and Martinell, B. J. 1993. Transformation of elite cotton cultivars via particle bombardment of meristems. Bio/technol. 11, 596-8.

Murray, E. E., DeBoer, D. L. and Firoozabady, E. 1993. Transgenic cotton. In "Transgenic Cotton", Vol 2, 153-68.

Murashige et al., 1962. A revised medium for rapid growth and bioassays with tobacco tissue cultures. Physiologia Plantarium 15, 473-97.

Perlak, F. J., Deaton, R. W., Armstrong, T. A., Fuchs, T. A., Sims, S. R., Greenplate, J. T. and Fischoff, D. A. 1990. Insect resistant cotton plants. Bio/technol. 8, 939-943.

Price, H. J. and Smith, R. H.1979. Somatic embryogenesis in suspension cultures of *Gossypium klotzschianum* Anderss. Planta 145, 305-6.

Rajasekaran, K., Grula, J. W., Hudspeth, R. L., Pofelis, S, and Anderson, D. M. 1996. Herbicide-resistant Acala and Coker cottons transformed with a native gene encoding mutant forms of acetohydroxyacid synthase. Mol. Breeding. 2, 307-19.

Rangan, F. J. and Zavala, T. Ip. A. 1984. Somatic embryogenesis in tissue culture of *Gossypium hirsutum* L.). In Vitro 20, 256.

Rangan, R. and Rajasekaran, K. 1996. Regeneration of cotton plant in cell suspension culture. U.S. Pat. No. 5,583,036 (continued from U.S. Pat. Nos. 5,244,802, 1993 and 122,200, 1987).

Ryals, J. 1996. Agricultural Biotechnology'96. Molecular Breeding 2, 91-93.

Schell, J. 1997. Cotton carrying the recombinant insect poison Bt toxin: no case to double the benefits of plant biotechnology.

Skovsted, A. 1935. Cytological studies in cotton. III. A hybrid between *Gossypium* davidsonii Kell, and G. sturrtii F. Muell. J. Genet. 30, 397405.

Stewart, J. McD. 1992. Biotechnology of cotton: achievements and perspectives. ICAC Review Articles on Cotton Production Research No. 3, 1-50.

Stewart, J. McD and Hsu, C. L. 1978. Hybridization of deploid and tetraploid cottons through in-ovulo embryo culture. J. Heridity 69, 404-8.

Srewart, J. McD. and Hsu, C. L., 1977. In ovulo embryo culture and seedling development of cotton (*Gossypium hirsutum* L.). Planta 137, 113-7.

Thomas, J. C., Adams, D. G., Keppene, V. D., Wasmann, C. C., Brown, J. K., Kanost, M. R. and Bohnert, H. J. 1995. Protease inhibitors of *Manduca sexta* expressed in transgenic cotton. Plant Cel, Rep. 14, 758-62.

Trolinder, N. L. 1985a. Somatic embryogenesis and plant regeneration in cotton (*Gossypium hirsutum* L.). A Dissertation in Biology (December, 1985).

Trolinder, N. L. 1985b. Genotype specificity of the somatic embryogenesis response in cotton. Plant Cell Reports 8, 133-6.

Trolinder, N. L. 1986. Somatic embryogenesis and plant regeneration in *Gossypium hirsutum* L. Dissertations Abstracts International 47, 2550B-2551B.

Trolinder, N. L. and Goodin, J. E. 1987. Somatic embryogenesis and plant regeneration in cotton (*Gossypium hirsutum* L.). Plant Cell Reports 6, 231-4.

Trolinder, N. L. and Goodin, J. E. 1988a. Somatic embryogenesis and regeneration in cotton. I. Effects of source of explant and hormone regime. Plant Cell Tissue Organ Culture 12, 31-42.

Trolinder, N. L. and Goodin, J. E. 1988b. Somatic embryogenesis and regeneration in cotton. II. Requirements for embryo development and plant regeneration. Plant Cell Tissue Organ Culture 12, 43-53.

Trolinder, N. L., Quisenberry, J., Bayley, C., Ray, C., and Ow, D. 1991. 2,4-D resistant transgenic cotton. Proc. Beltwide Cotton Prod. Res. Conf., 840.

Turaev, A. M. and Shamina, Z. B. 1986. Soniet Plant Physiol. 33, 439.

Umbeck, P. F., 1991. Genetic engineering of cotton plants and lines. U.S. Pat. No. 5,004,863.

Umbeck, P. F. 1992. Genetic engineering of cotton plants and lines. U.S. Pat. No. 5,159,135 (continued from U.S. Pat. No. 5,004,863, 1991).

Umbeck, P. F, Johnson, G., Barton, K. and Swain, W. 1987. Genetically transformed cotton (*Gossypium hirsutum* L.) plants. Bio/technol. 5, 263-6.

Umbeck, P. F., Swain, W. and Yang, N.-S., 1989. Inheritance and expression of genes for kanamycin and chloramphenical resistance in transgenic cotton plants. Crop. Sci. 29, 196-201.

Valvekens, D., Van Montagu, M., Van Lijsebettens, M. 1988. *Agrobacterium tumefaciens*-mediated transformation of *Arabidopsis* root explants by using kanamycin selection. Proc. Natl. Acad. Sci. USA 85, 5536-40.

Walkerpeach, C. R. and Veltern, J. 1994. *Agrobacterium*-mediated gene transfer to plant cells: cointegrate and binary vector systems. Plant Mol. Biol. Mannuel B1, 1-19.

Zhang, H.-B. 1994. The tissue culture of cotton (II). Plant Physiol. Commun. 30, 386-91.

Zhang, H.-B. and Feng, R. 1992. The tissue culture of cotton (I). Plant Physiol. Commun. 30, 386-91.

Zhou, G.-Y., Weng, J., Zeng, Y.-S., Huang, J.-G., Qian, S.-Y. and Liu, G.-L. 1983. Introduction of exogenous DNA into cotton embryos. Methods in Enzymology 101, 433-81.

We claim:

1. A method for producing a transgenic cotton plant comprising:
    (a) preparing explants from fibrous roots of cotton seedlings cultured in medium comprising about 0.05 mg/l to 0.2 mg/l of multi-effect triazole (MET);
    (b) culturing said root explants in medium comprising a plant hormone selected from the group consisting of (I) (2,4-dichlorophenoxy)acetic acid (2,4-D), (ii) 6-γγ-dimethylallyl(amino) purine (2iP), (iii) a mixture of 2,4-D and kinetin and (iv) a mixture of 2iP and α naphthalene acetic acid to induce callus formation;
    (c) transforming said callus with *Agrobacterium tumifaciens* comprising a first DNA encoding a chimeric gene of interest to effect the stable transfer of said chimeric gene to the genome of cells comprising the callus tissue;
    (d) culturing said transformed callus to induce somatic embryos and development of plantlets from said somatic embryos; and
    (e) rooting said plantlets to produce transgenic cotton plants having said gene of interest.

2. The method of claim 1 wherein the concentration of the MET is about 0.1 mg/l.

3. The method of claim 1 wherein the medium in step (a) further comprises about 0.01 to 0.2 mg/l of α naphthalene acetic acid (NAA).

4. The method of claim 3 wherein the concentration of NAA is 0.05 mg/l.

5. The method of claim 1 wherein step (e) is carried out in the presence of about 0.05 to 0.2 mg/l of MET.

6. The method of claim 5 wherein the concentration of the MET is 0.1 mg/l.

7. The method of claim 5 wherein step (e) is further carried out in the presence of about 0.01 to 0.2 mg/l α naphthalene acetic acid (NAA).

8. The method of claim 1 wherein the concentration of NAA is 0.05 mg/l.

9. The method of claim 1 wherein step (b) is carried out in a callus inducing culture medium comprising myo-inositol, vitamin $B_1$ and 2iP.

10. The method of claim 1 wherein step (d) is carried out in a somatic embryo inducing culture medium comprising myo-inositol, vitamin $B_1$ and 2iP.

11. The method of claim 9 wherein the callus inducing culture medium comprises from about 50 to 150 mg/L of myo-inositol, from about 0.2 to 10 mg/L vitamin $B_1$ and from about 0.1 to 7.5 mg/L 2iP.

12. The method of claim 11 wherein the callus inducing culture medium comprises 100 mg/L myo-inositol, 0.4 mg/L vitamin $B_1$ and 5 mg/L 2iP.

13. The method of claim 10 wherein somatic embryo inducing culture medium comprises from about 50 to 100 mg/L myo-inositol, from about 0.2 to 10 mg/L vitamin $B_1$ and from about 0.1 to 0.5 mg/L 2iP.

14. The method of claim 13 wherein somatic embryo inducing culture medium comprises 100 mg/L myo-inositol, 0.4 mg/L vitamin $B_1$ and 5 mg/L 2iP.

15. The method of claim 1 wherein step (b) is carried out in a callus inducing culture medium comprising vitamin $B_5$, 2,4-D, $MgCl_2$ and glucose.

16. The method of claim 1 wherein step (d) is carried out in a somatic embryo inducing culture medium comprising vitamin $B_5$, 2,4-D, $MgCl_2$ and glucose.

17. The method of claim 15 wherein the callus inducing culture medium comprises from about 0.2 to 10 mg/L vitamin $B_5$, from about 0.05 to 0.15 mg/L 2,4-D, from about 0.4 to 1.2 mg/L, $MgCl_2$ from about 1% to 5% glucose.

18. The method of claim 17 wherein the callus inducing culture medium comprises 0.4 mg/L vitamin $B_5$, 0.1 mg/L 2,4-D, 0.8 mg/L $MgCl_2$ and 3% glucose.

19. The method of claim 16 wherein the somatic embryo inducing culture medium comprises from about 0.2 to 10 mg/L vitamin $B_5$, from about 0.05 mg/L to 0.15 mg/L 2,4-D, from about 0.4 to 1.2 mg/L, $MgCl_2$ from about 1% to 5% glucose.

20. The method of claim 19 wherein the somatic embryo inducing medium comprises 0.4 mg/L vitamin $B_5$, 0.1 mg/L 2,4-D, 0.8 mg/L $MgCl_2$ and 3% glucose.

21. A method according to claim 1, wherein the medium of steps (a), (b), (c), (d) or (e) further comprises from about 1.0 g/L to 3.0 g/L gellan gum.

22. The method of claim 1 wherein the step of inducing somatic embryo culture is carried out in a somatic embryo-inducing medium comprising a nitrate in an amount from about 1900 to 5700 mg/L.

23. A method according to claim 22, wherein the nitrate is $KNO_3$.

24. The method of claim 1 wherein said DNA is selected from the group consisting of an herbicide resistance gene, a gene that confers glyphosate resistance, a shikimate synthase gene and a *Bacillus thuringiensis* toxin gene.

25. The method of claim 1 wherein said *Agrobacterium tumifaciens* further comprises a second DNA encoding a selectable marker gene to effect the stable transfer of said selectable marker gene to the genome of cells comprising the callus tissue.

26. The method of claim 1, wherein said seedlings are seedlings of *Gossypium hirsutum* cv. *Coker* 312.

27. The method of claim 22, wherein the amount of nitrate is about 3800 mg/L.

28. A method according to claim 27, wherein the nitrate is $KNO_3$.

29. A method for producing a transgenic cotton plant comprising:
(a) germinating seeds by culturing on medium comprising about 0.05 mg/l to 0.2 mg/l of multi-effect triazole (MET) and about 0.01 to 0.2 mg/l of a naphthalene acetic acid (NAA) to produce seedlings with fibrous roots;
(b) culturing fibrous roots on medium comprising a plant hormone selected from the group consisting of (I) (2,4-dichlorophenoxy)acetic acid (2,4-D), (ii) 6-γγ-dimethylallyl(amino) purine (2iP), (iii) a mixture of 2,4-D and kinetin and (iv) a mixture of 2iP and α naphthalene acetic acid to prepare fibrous roots for culturing with *Agrobacterium tumifaciens*;
(c) transforming the prepared fibrous roots by incubating the fibrous roots with a cell suspension of *Agrobacterium tumifaciens* comprising a first DNA encoding a chimeric gene of interest to effect the stable transfer of said chimeric gene to the genome of cells of the fibrous roots;
(d) culturing the transformed fibrous roots on medium comprising a plant hormone selected from the group consisting of (I) (2,4-dichlorophenoxy)acetic acid (2,4-D), (ii) 6-γγ-dimethylallyl(amino) purine (2iP), (iii) a mixture of 2,4-D and kinetin and (iv) a mixture of 2iP and α naphthalene acetic acid to produce cultured transformed fibrous roots;
(e) culturing the cultured transformed fibrous roots on medium comprising a plant hormone selected from the group consisting of (I) (2,4-dichlorophenoxy)acetic acid (2,4-D), (ii) 6-γγ-dimethylallyl(amino) purine (2iP), (iii) a mixture of 2,4-D and kinetin and (iv) a mixture of 2iP and α naphthalene acetic acid to induce callus formation;
(f) culturing the callus to induce somatic embryos and development of plantlets from said somatic embryos; and
(g) rooting said plantlets to produce transgenic cotton plants having said gene of interest.

30. The method of claim 29 wherein said *Agrobacterium tumifaciens* further comprises a second DNA encoding a selectable marker gene to effect the stable transfer of said selectable marker gene to the genome of cells of the fibrous roots.

31. The method of claim 29, wherein said seeds are seeds of *Gossypium hirsutum* cv. Coker 312.

* * * * *